US006514994B2

(12) United States Patent
Mather et al.

(10) Patent No.: US 6,514,994 B2
(45) Date of Patent: *Feb. 4, 2003

(54) LEVOBUPIVACAINE AND ITS USE

(75) Inventors: Laurence E. Mather, Sydney (AU); Andrew John McGlashan Richards, Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/969,412

(22) Filed: Oct. 1, 2001

(65) Prior Publication Data

US 2002/0016338 A1 Feb. 7, 2002

Related U.S. Application Data

(63) Continuation of application No. 09/481,635, filed on Jan. 12, 2000, now abandoned, which is a continuation of application No. 09/120,822, filed on Jul. 22, 1998, now Pat. No. 6,069,155.

(30) Foreign Application Priority Data

Jul. 22, 1997 (GB) ............................................. 9715462
Oct. 17, 1997 (GB) ............................................. 9722022
May 14, 1998 (GB) ............................................. 9810427

(51) Int. Cl.$^7$ ............................................. A61K 31/445

(52) U.S. Cl. ............................................. 514/330

(58) Field of Search ............................................. 514/330

(56) References Cited

U.S. PATENT DOCUMENTS

| | | | | |
|---|---|---|---|---|
| 4,695,576 A | | 9/1987 | af Ekenstam et al. | ...... 514/330 |
| 6,103,741 A | * | 8/2000 | Bardsley et al. | ............ 514/330 |

FOREIGN PATENT DOCUMENTS

| | | |
|---|---|---|
| WO | 9632109 | 10/1996 |

OTHER PUBLICATIONS

Butterworth, J.F. (1993) "Bupivacaine Inhibits Cyclic–3', 5'–Adenosine Monophosphate Production" *Anesthesiology* 79:88–95.
Mazoit, J.X. et al. (1983) "Myocardial Uptake of Bupivacaine: II. Pharmacokinetics and Pharmacodynamics of Bupivacaine Enantiomers in the Isolated Perfused Rabbit Heart" *Anesth. Anal.* 77(3):477–482.
Clarkson, C.W., L.M. Hondeghem (1985) " Mechanism for Bupivacaine Depression of Cardiac Conduction: Fast Block of Sodium Channels during the Action Potential with Slow Recovery from Block during Diastole" *Anesthesiology* 62:396–405.
Courtney, K.R., J.J. Kendig (1988) "Bupivacaine is an effective potassium channel blocker in heart" *Biochimica et Biophysica Acta* 939:163–166.

Denson, D.D., M.M Behbehani, R.V. Gregg (1992) "Enantiomer–Specific Effects of an Intravenously Administered Arrhythymogenic Dose of Bupivacaine on Neurons of the Nucleus Tractus of Solitarius and the Cardiovascular System in the Anesthetized Rat" *Regional Anesthesia* 17(6):311–316.
Vanhoutte, F. et al. (1991) "Stereoselective effects of the enantiomers of bupivacaine on the electrophysiological properties of the guinea–pig papillary muscle" *Br. J. Pharmacol.* 103:1275–1281.
Valenzuela, C. et al. (1994) "Stereoselective Bupivacaine Block of the Human Cardiac Delayed Rectifier Kv1.5 Channel" *Biophys. J.* 66:A205; abstract No. Tu–Pos383.
Aps, C., F. Reynolds (1978) "An Intradermal Study of the Local Anaesthetic and Vascular Effects of the Isomers of Bupivacaine" *J. Clin. Pharmac.* 6:63–68.
Burm, A.G.L. et al. (1994) "Pharmacokinetics of the enantiomers of bupivacaine following intravenous administration of the racemate" *Br. J. Clin. Pharmac.* 38:125–129.
Reynolds, F. (1995) "In defence of bupivacaine" *International Journal of Obstetric Anesthesia* 4(2):93–108.
Rutten, A. J. et al. (1993) "Tissue Distribution of Bupivacaine Enantiomers in Sheep" *Chirality* 5(7):485–491.
Aberg, G. (1972) "Toxicological and Local Anaesthetic Effects of Optically Active Isomers of Two Local Anaesthetic Compounds" *Acta Pharmacologica Et Toxicologica* 31:273–286.
Testa, B., W.F. Trager (1990) "Racemates Versus Enantiomers in Drug Development: Dogmatism or Pragmatism?" *Chirality* 2:129–133.
Ariëns, E.J. (1991) "Racemic therapeutics—ethical and regulatory aspects" *Eur. J. Clin. Pharmacol.* 41(2):89–93.
Rutten, A.J., L.E. Mather, C.F. McLean (1991) Cardiovascular Effects and Regional Clearances of I.V. Bupivacaine in Sheep: Enantiomeric Analysis. *Br. J. Anaesthesia* 67:247–256.
Luduena, F.P., E.F. Bogado, B.F. Tullar (1972) "Optical Isomers of Mepivacaine and Bupivacaine" *Arch. Int. Pharmacodyn* 200(2):359–369.
Rutten, A.J. et al. (1992) "Postoperative course of plasma protein binding of lignocaine, ropivacaine and bupivacaine in sheep" *J. Pharm. Pharmacol.* 44:355–358.
Lee–Son, S. et al. (1992) "Stereoselective Inhibition of Neuronal Sodium Channels by Local Anesthetics" *Anesthesiology* 77(2):324–335.
Wang, G.K. et al. (1992) "Altered Stereoselectivity of Cocaine and Bupivacaine Isomers in Normal and Batrachotoxin–modified Na+ channels" *J. Gen. Physiol.* 100(6):1003–1020.

(List continued on next page.)

Primary Examiner—Phyllis G. Spivack
(74) Attorney, Agent, or Firm—Saliwanchik, Lloyd & Saliwanchik

(57) ABSTRACT

A unit dosage and pharmaceutical delivery system for anaesthetizing a human patient prior to major surgery, which comprise between 200 mg and 300 mg of levobupivacaine.

7 Claims, 2 Drawing Sheets

OTHER PUBLICATIONS

Luduena, F.P., B.F. Tullar (1970) "Optical isomers of an aminoacyl xylidide" *Chemical Abstracts* 73(5); abstract No. 25314a.

Clark, B.J., A. Hamdi (1991) "Reversed–phase and chiral high–performance liquid chromatographic assay of bupivacaine and its enantiomers in clinical samples after continuous extraplural infusion" *Journal of Chromatography* 553:383–390.

Ariëns, E.J. (1990) "Racemische therapeutica probleemmiddelen" *Pharmaceutisch Weekblad* 125(2):552–554.

Ariëns, E.J. (1990) "Stereoselectivity in pharmacodynamics and pharmacokinetics" *Schweiz. Med. Wochenschr* 120(5):131–134.

Gristwood, R. et al. (1994) "Reduced cardiotoxicity of levobupivacaine compared with racemic bupivacaine (Marcaine): new clinical evidence" *Exp. Opin. Invest. Drugs* 3(11):1209–1212.

Albright, G.A. (1979) "Cardiac Arrest Following Regional Anesthesia with Etidocaine or Bupivacaine" *Anesthesiology* 51:285–287.

Prentiss, J.E. (1979) "Cardiac Arrest Following Caudal Anesthesia" *Anesthesiology* 50(1):51–53.

Moore, D.C. et al. (1976) "Arterial and Venous Plasma Levels of Bupivacaine Following Epidural and Intercoastal Nerve Blocks" *Anesthesiology* 45(1):39–45.

Moore, D.C. et al. (1976) "Arterial and Venous Plasma Levels of Bupivacaine Following Peripheral Nerve Blocks" *Anesthesia and Analgesia . . . Current Researches* 55(6):763–768.

Moore, D.C. et al. (1977) "Bupivacaine (Marcaine): An Evaluation of its Tissue and Systemic Toxicity in Humans" *Acta Anesth. Scand.* 21:109–121.

Kuhnert, B.R. et al. (1981) "Bupivacaine disposition in mother, fetus and neonate" *Federation Proceedings* 40(31):684.

Rowland, M., T.N. Tozer, eds. (1995) Clinical Pharmacokinetics Concepts and Applications; Williams & Wilkins; (Chapter 7):83–88.

Mather, L.E. (1991) "Dispositon of Mepivacaine and Bupivacaine Enantiomers in Sheep" *British Journal of Anaesthesia* 67:239–246.

DuPen, S.L. et al. (1992) "Chronic epidural bupivacaine—opioid infusion in intractable cancer pain" *Pain* 49:293–300.

Honerjäger, P. (1986) "The contribution of Na channel block to the negative inotropic effect of antiarrhythmic drugs" *Basic Res. Cardiol.* 81(Suppl 1):33–37.

Fozzard, H.A., J.A. Wasserstrom (1985) "Voltage Dependence of Intracellular Sodium and Control of Contraction" In Zipes D.P., E. Jalife (eds) Grune & Stratton, Orlando; 51–57.

Schlepper, M. (1989) "Cardiodepressive effects of antiarrhythmic drugs" *European Heart Journal* 10(Suppl E):73–80.

Reiz, S., S. Nath (1986) "Cardiotoxicity of Local Anaesthetic Agents "Br. J. Anaesth. 58:736–746.

DeJong, R. H., N. L. Davis (1981) "Treating Bupivacaine Arrhythmias" *Reg. Anesth.* 6:99–103.

Strichartz, G.R. (1988) "Neutral physiology and local anesthetic action" In: Neural Blockage in Clinical Anesthesia and Management of Pain. Cousins, J.J., P.O. Bridenbaugh (eds), J.B. Lippincott Company, Philadelphia; 25–45.

* cited by examiner

LEVOBUPIVACAINE AND ITS USE

CROSS REFERENCE TO A RELATED APPLICATION

This application is a continuation of application Ser. No. 09/481,635, filed Jan. 12, 2000 abandoned; which is a continuation of application Ser. No. 09/120,822, filed Jul. 22, 1998 U.S. Pat. No. 6,069,155.

FIELD OF THE INVENTION

This invention relates to a new therapeutic use for levobupivacaine or (S)-1-butyl-N-(2,6-dimethylphenyl)-2-piperidinecarboxamide, and to new formulations including it.

BACKGROUND OF THE INVENTION

Racemic bupivacaine is an effective long-acting local anaesthetic, and may be given as an epidural. However, racemic bupivacaine is cardiotoxic, having depressant electrophysiological and mechanical effects on the heart. It should therefore be used with caution in cardiac-compromised patients, and the use of high doses and high concentrations is contraindicated.

In particular, bupivacaine has produced death in a number of patients, including women in childbirth and when used in the Bier's block technique. Although the incidence of death has been relatively small, the concern has been sufficient to stop the use of 0.75% bupivacaine for obstetrics and the proscribing of bupivacaine for use in Bier's blocks.

In addition, due to its mode of action, directly on the nervous system, at higher doses, bupivacaine is known to have undesirable central nervous system (CNS) side-effects which, prima facie, are connected to its anaesthetic activity. Indeed, the occurrence of CNS side-effects is one of the major factors limiting the use of this drug in normal clinical practice employing techniques such as local infiltration, nerve block field block, epidural and spinal blocks.

It has been suggested that levobupivacaine is less cardiotoxic than dextrobupivacaine and racemic bupivacaine. See, for example, Vanhoutte et al, Br. J. Pharmacol. 103:1275–1281 (1991), and Denson et al, Regional Anaesthesia 17:311–316 (1992). However, these reports are based on work in vitro, and cannot necessarily be extrapolated to any mammals, and certainly not to humans.

The effective utility of levobupivacaine in man, in vivo, is evidenced for the first time in WO-A-9510276, WO-A-9510277 and Gristwood et al, Exp. Opin. Invest. Drugs 3(11):1209–12 (1994). The latter documents indicate the potential utility of levobupivacaine in obstetrics, in part at least because of reduced CNS side-effects.

Gristwood et al also disclose that bupivacaine has "a beneficial ratio of sensory to motor blockade. This ratio is particularly important for obstetric use as it affords appropriate sensory block and yet allows women to consciously participate in the childbirth". Gristwood et al then report experiments comparing bupivacaine and levobupivacaine, and conclude that a "preliminary analysis of the data suggests that in terms of sensory block, levobupivacaine has comparable efficacy to bupivacaine, with the duration of sensory block for 0.25% levobupivacaine being similar to that seen with bupivacaine 0.25%".

WO-A-9500148 discloses that ropivacaine salts provide sensory block and "minimal motor blockade". It is suggested that this effect is desirable, because reduced motor blockade (compared to bupivacaine) allows the patient to move, say, legs soon after operation.

There are of course many more major surgical procedures, where profound block is required, the need is for administration of high amounts and volumes of anaesthetic, and where safety is a major consideration. Although racemic bupivacaine is an effective long-acting anaesthetic, large doses may be toxic. Further, particularly when administered as a bolus injection, where there is a real risk of accidentally administering the drug to the wrong site, safety is a critical consideration. For example, there is a risk of intravascular injection, in abdominal surgery, brachial plexus and femoral sciatic nerve blocks.

SUMMARY OF THE INVENTION

This invention is based on two surprising observations. The first is that, whereas a large dose of bupivacaine may be fatal in sheep, the same dose of levobupivacaine is not. It is therefore possible to administer much larger amounts of levobupivacaine, safely. Without wishing to be bound by theory, it may be that, because a given dose of levobupivacaine takes longer to reach $T_{max}$ than the same dose of racemate, a higher amount of levobupivacaine may safely be administered, that provides anaesthesia.

The second observation is that levobupivacaine exhibits a different pathic handling compared with bupivacaine. This manifests itself as a faster plasma clearance rate within 0–4 hours post-administration. Therefore, for major surgical procedures, where aberrant injection may occur, the risk of harming the patient is reduced due to faster clearance in the problematic phase.

In accordance with the present invention, levobupivacaine is administered as an anaesthetic for major surgery in an amount that could not be used by injection, with confidence, for bupivacaine, i.e. at least 200 mg, often at least 225 mg, and perhaps more than 250 mg, e.g. up to 300 mg. A novel unit dosage or delivery system, e.g. a syrnge, may comprise such an amount of the drug. In terms of the amount of drug administered, this may be at least 3 mg/kg.

DESCRIPTION OF THE INVENTION

Figure 1:
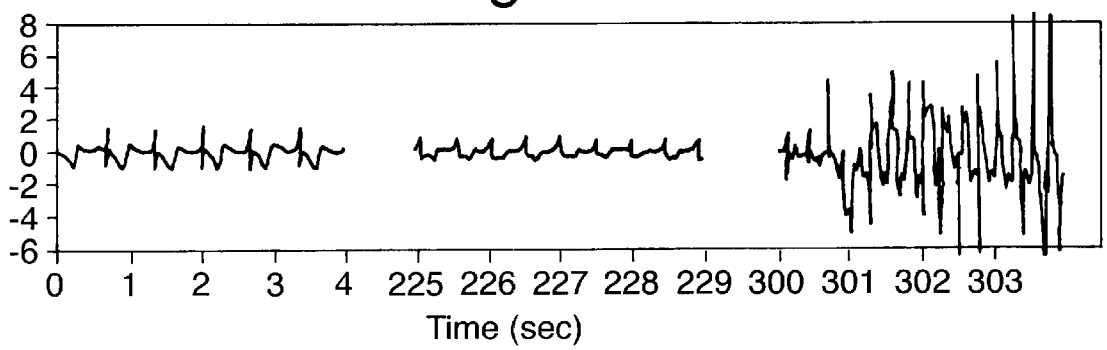
FIGS. 1 and 2 show baseline record of ECG (left), S-T segment change (center) and multiform ventricular tachycardia (right) after i.v. infusion (40 ml, 3 min) of 100 mg bupivacaine and then of 200 mg levobupivacaine, in the same sheep.

There are various embodiments of major surgery, in which levobupivacaine is suitably used, according to this invention (but which may exclude known uses). They include major orthopaedic and abdominal surgery, shoulder and facial surgery, and as an analgesic in plastics/burns procedures. Typical blocks may be brachial plexus, axillary, supraclavicular block or interscalene.

These procedures are characterised by the desire or need for deep sensory block and adequate motor block.

In the method of the present invention, levobupivacaine may be provided in solution, for infusion or injection, or for administration by any of the conventional means for obtaining a nerve or field block/local infiltration. In addition to the anaesthetic blocks conventionally provided by the racemate, levobupivacaine may also be useful in providing blocks in areas of the body where the risk of systemic exposure to the drug, and therefore CNS side-effects, is particularly high. Examples include open wounds and vascular areas, for instance using intercostal blocks for the latter.

For upper limb surgery at least, infusion into the body near the base of the limb may be appropriate. A regional or plexus block may also be used.

Administration of levobupivacaine may be continuous or bolus administration. This may be done using conventional apparatus, e.g. including means for the patient to induce infusion as desired. Administration may also be by infiltration.

The concentration of levobupivacaine to be given can be that conventionally used for the racemic drug, e.g. 0.5% v/v. However, the concentration is typically higher than this, for instance, at least 0.75% w/v, and can be up to 2% w/v. Thus, the concentration of levobupivacaine may be in the range 0.8% to 1.5% w/v, e.g. 1%, 1.25% or 1.5% w/v is used.

In certain instances, it may be preferred to use no more than 0.5% w/v levobupivacaine. This concentration may provide less motor block than a higher concentration, or the same concentration of racemate, when administered epiduraly, e.g. for lower limb surgery. However, a higher concentration may increase depth and duration of sensory block.

Levobupivacaine administered spinally has advantages, in terms of reduced neurotoxicity, over lignocaine (whether plain or hyperbaric formulations). Lignocaine must typically be administered at a concentration of 2–5%. Racemic bupivacaine is not widely used for spinal administration.

The solution may typically be put up in unit doses of from 1 to 15 ml, and preferably of around 10 ml. However, the unit doses may be higher, for instance up to 40 ml or higher, for instance in some nerve blocks or via local infiltration. The unit doses may be in the form of ampoules, which may be made of any suitable material, eg. glass or an appropriately impervious plastic material. Unit dosages comprising at least 200 mg of levobupivacaine are new and can be used directly. The amount administered may be 3 to 5 mg/kg.

The administration of levobupivacaine over a range of concentrations, including those currently used for the racemic drug and the higher concentrations described above, can be carried out for significantly longer periods than at present, again as a result of the reduced CNS side-effects experienced with levobupivacaine. For instance, levobupivacaine can be administered to a patient safely for at least 24 hours, often up to 72 hours, and even for periods of up to a week or a fortnight, or longer. It can, of course, be administered for similar periods already used for the racemic drug, e.g. between 3 and 6 hours.

If desired, levobupivacaine can be administered with another drug such as fentanyl; see PCT/GB98/00658.

The levobupivacaine used in the present invention is preferably substantially free of dextrobupivacaine, and is more preferably in at least 90%, and most preferably at least 99%, enantiomeric excess with respect to dextrobupivacaine. Throughout this specification, reference to bupivacaine and its enantiomers includes pharmaceutically-acceptable salts thereof.

The following Studies provide evidence, on which this invention is based.

Study 1

The electrocardiological effects of bupivacaine and levobupivacaine were compared, in two groups of conscious, previously instrumented, adult sheep. Two cohorts of 7 animals were infused over 1 min with 6.25, 12.5, 18.75, 25 and 37.5 mg levobupivacaine and 12.5, 25 and 37.5 mg bupivacaine or over 3 min with 37.5, 50, 75, 100, 150 and 200 mg levobupivacaine and 37.5, 75, 100, 150 and 200 mg bupivacaine. Both drugs at doses of 75 mg were without significant electrocardiological effect. Both drugs, at convulsive doses (75 mg bupivacaine, 100 mg levobupivacaine), induced ventricular arrhythmias; however, there was a higher threshold of toxicity with levobupivacaine. Significantly fewer, as well as less deleterious, ventricular arrhythmias were induced with levobupivacaine compared with the same doses of bupivacaine. Three animals died within 10 min of 150, 150 and 200 mg bupivacaine, respectively, from the sudden onset of ventricular tachycardia and resultant ventricular fibrillation. No animals died whilst receiving the same dose of levobupivacaine on a previous occasion on which arrhythmias occurring automatically returned to sinus rhythm. These results indicate that bupivacaine is inherently more arrhythmogenic than levobupivacaine in conscious sheep. Inasmuch as levobupivacaine is reported to produce at least equivalent neural blockade to bupivacaine, it therefore offers a great margin of clinical safety.

Figure 2:
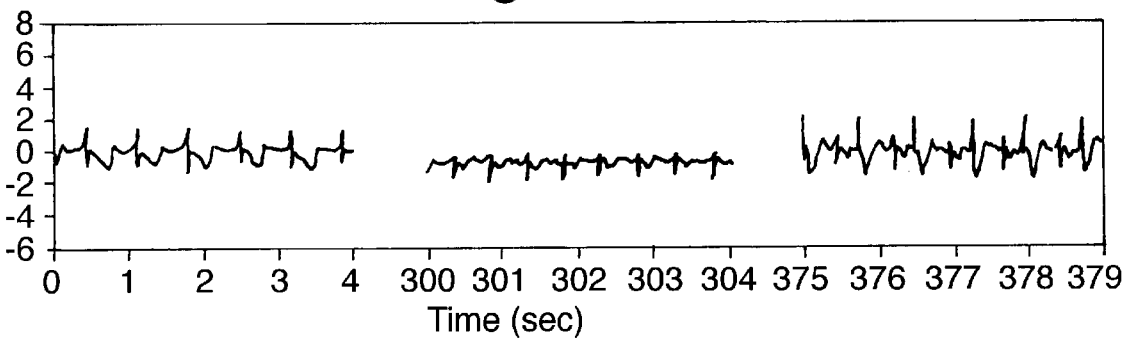

FIGS. 1 and 2 of the accompanying drawings show baseline record of ECG (left), S-T segment change (centre) and multiform ventricular tachycardia (right) after i.v. infusion (40 ml, 3 min) of 100 mg bupivacaine and then of 200 mg levobupivacaine, in the same sheep.

Bupivacaine was slightly more potent in inducing an arrhythmia; it was more than three times more potent in sustaining the arrhythmia.

Study 2

Reiz et al, Acta Anaesthesiol. Scand. (1989) 33:93–98, reports that in vivo cardiotoxicity of local anaesthetics can be evaluated without interference by central mechanisms in a highly reproducible model (Pentobarbital-Anesthetized Swine) where the drug is injected directly into a coronary artery. When local anesthetics are injected in the left anterior descending artery (LAD), death occurs consistently by ventricular fibrillation (VF). The aim of this study was to determine the lethal dose of each of the local anesthetics levobupivacaine (L), bupivacaine (B) and ropivacaine (R) as well as to compare their respective effects on the QRS interval of the precordial ECG. Prolongation of the QRS has been shown to correlate highly with in vitro cardiotoxicity of bupivacaine and lidocaine (Reiz et al, supra).

A total of 27 animals were randomized to receive a dose response injection of L, B or R into the LAD. A blinded randomized protocol was used. All calculations and exclusions were made prior to disclosure of treatment. The doses of each agent were 0.375, 0.75, 1.5, 3.0, 4.0 mg etc., in increments of 1 mg till death occurred. Each dose was made up in a volume of 3 ml plus the dead space of the catheter (1.2 ml), injected over 10 sec. The time between doses was 5 min, or longer, if ECG, blood pressure or heart rate had not returned to pre-injection controls. A complete 12-lead ECG was recorded on optical disk for later analysis. Statistical analysis was by ANOVA, Dunnett's and the Mann-Whitney-U test. Power analysis was performed (0.85 to 1.00).

One animal died of myocardial infarction following acute embolization into the LAD. Of the 26 remaining animals, 6 were found to have been injected into the right coronary artery (RCA) following undetected reversal of the radiological image during coronary artery catheterization. Of the animals injected into the LAD, 7 had received L, 7 B and 6 R. All deaths following LAD injection were by VF and deaths following RCA injection were by A-V dissociation. The lethal doses of L (median 8 mg, range 7–9 mg) and R (median 8 mg, range 4–10 mg) were significantly higher (p<0.01 and 0.05 respectively) than that of bupivacaine (median 5 mg, range 4–6 mg). Death following RCA injection was within the same dose ranges and did not alter the difference between drugs. QRS prolongation was plotted versus log dose of each drug and revealed results for B and R identical to those previously obtained in the same model. In contrast to L and B, R did not produce more than 100% (approximately 60 msec) QRS prolongation (at the 6 mg dose). To obtain the same degree of QRS prolongation, L had to be given in a significantly higher dose than B. The difference was 25% at 40 msec QRS prolongation and 47% at 90 msec QRS prolongation. The difference between L and R at 50 msec prolongation was insignificant.

This study showed that the lethal doses of L and R were approximately 50% higher than that of B, regardless of whether the drugs were injected into the LAD or RCA causing death by VF or A-V dissociation. A similar difference between the drugs was observed for the doses producing comparable QRS prolongation.

Study 3

This study compared the efficacy, safety and pharmacokinetics of 0.75% levobupivacaine with 0.75% bupivacaine in 58 patients undergoing major abdominal surgery under epidural anaesthesia. Although 0.75% bupivacaine is no longer used in some situations (obstetrics) and 0.5% concentrations are usually adequate for lower extremity surgery, 0.75% is preferential for abdominal surgery because of the enhancement of motor blockade. Onset of sensory anaesthesia to T10 (mean~15 minutes), time to peak block height (T5, 25–30 min), and abdominal muscle relaxation (RAM score 3–5) were equivalent between the groups. Duration of total sensory anaesthesia was statistically longer with 0.75% levobupivacaine (levobupivacaine—551 min, racemic bupivacaine—506 min). This shows that the improvement in safety is highly relevant.

Study 4

Contraction was measured in mycocytes and papillary muscle isolated from guinea-pig ventricle and pectinate muscle isolated from human right atrial appendage.

Myocytes were isolated from guinea-pig left ventricle by an enzyme digestion procedure and placed in a chamber on the stage of an inverted microscope. Cells were superfused with Krebs-Henseleit buffer (KHB) at 30° C. and field stimulated at 1.0 Hz. Cell shortening was measured with a video camera and edge-etection system. Papillary and pectinate muscles were placed in KHB at 37° C. and field stimulated at 1.0 Hz. Isometric tension was recorded at maximum developed force ($L_{max}$).

Electrophysical parameters were recorded in papillary muscles superfused with KSB at 37° C. and stimulated at 1.0 Hz. Standard action potential parameters were recorded, i.e. maximum rate of rise of membrane potential ($V_{max}$); action potential amplitude (APA); and action potential duration to 90% repolarisation ($APD_{90}$). Developed force was measured by recording isometric tension in muscles stretched to 90% of $L_{max}$.

The effect of equimolar concentrations of levobupivacaine, bupivacaine and ropivacaine on developed force and action potential parameters were measured at steady-state. No significant differences were noted.

The mean drug concentration producing a 50% reduction (CI-50) in cell shortening was calculated from cumulative dose-response curves. All data were analysed by an unpaired t-test (for control data comparison) or one-way ANOVA (for comparison between drug groups), assuming a Gaussian distribution.

Figure 3:
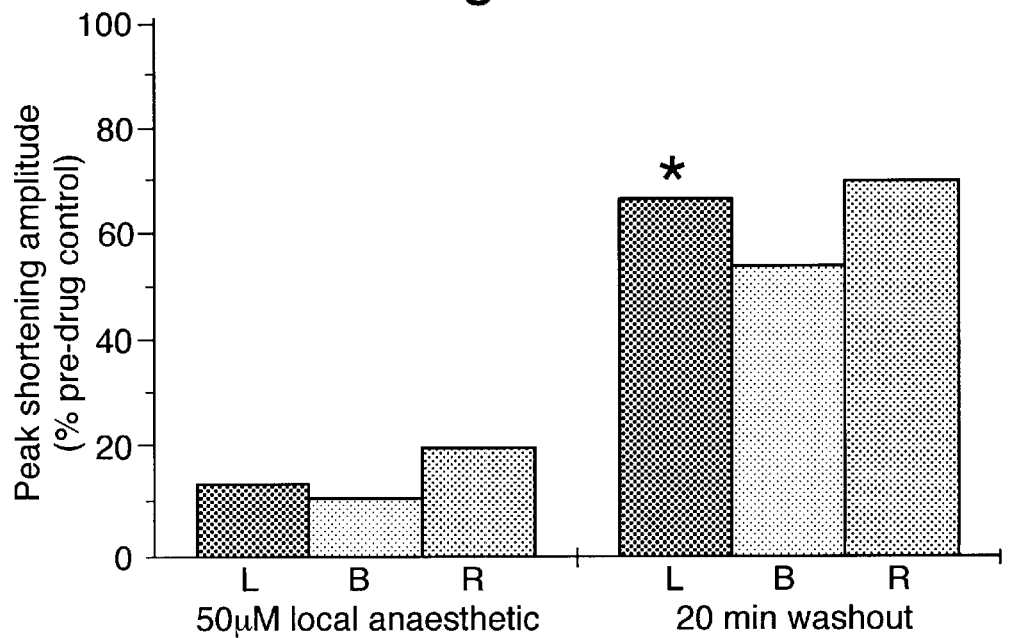
FIG. 3 shows that, on washout of local anaesthetic from myocardium with drug-free perfusate, the recovery of contractility following levobupivacaine was significantly greater than that for bupivacaine (P<0.05) in cardiac mycocytes.
Figure 4:
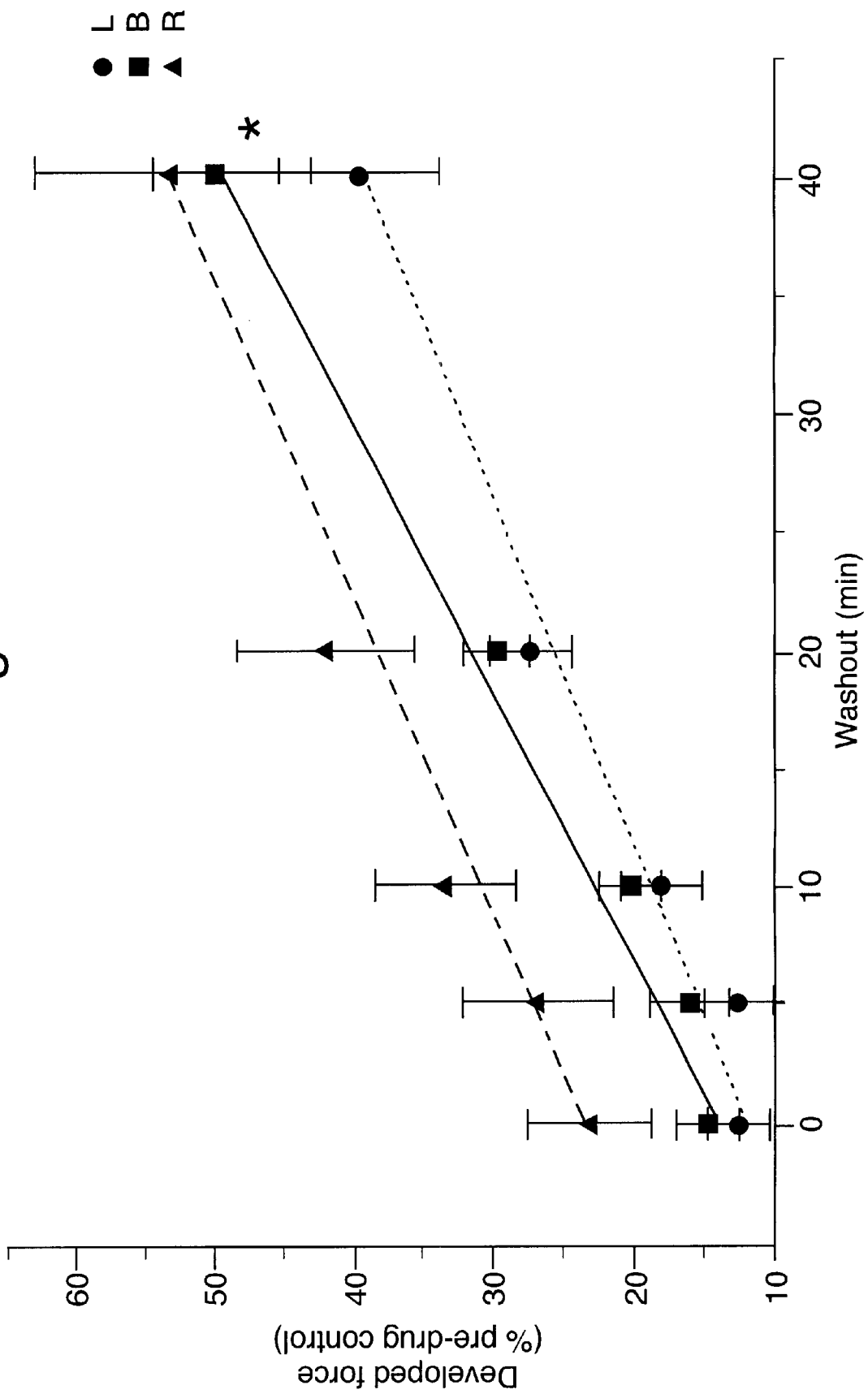
FIG. 4 shows that, on washout of local anaesthetic from myocardium with drug-free perfusate, the recovery of contractility following levobupivacaine was significantly greater than that for bupivacaine (P<0.05) in guinea-pig papillary muscle.

The most important observation was that, on washout of local anaesthetic from myocardium with drug-free perfusate, the recovery of contractility following levobupivacaine was significantly greater than that for bupivacaine (P<0.05) in both cardiac mycocytes (see FIG. 3) and guinea-pig papillary muscle (see FIG. 4). Therefore, there is a potential for better reversibility after intravascular injection of levobupivacaine.

Study 5

20 adult patients scheduled for distal upper extremity orthopaedic surgical procedures with axillary brachial plexus neural blockade were studied. Patients received an axillaryblock using 50 ml of 0.5% levobupivacaine without epinephrine. Transarterial and/or nerve stimulator techniques were used to identify injection into the brachial plexus sheath. If after 10 min patients required supplemental local anaesthetic to produce anaesthesia in a single peripheral nerve distribution, an additional 10 ml of 0.5% levobupivacaine could be administered as a single peripheral nerve-block at the axilla or wrist. Patients were monitored for onset and duration of sensory and motor block using a 0–2 scale (0=no block, 1=partial block, 2=complete block) for each major nerve distribution (median, musculocutaneous, radius, ulnar). Time to onset of adequate anaesthesia for surgery, time to first request for post-operative analgesics, as well as any subjective or objective signs of local anaesthetic toxicity were also collected. Blood samples for PK analysis were drawn from 10 patients.

The patients ranged in age from 20–81 years, and body weight was 50–107 kg. Doses of 50–60 ml of levobupivacaine in these patients ranged from 3–5 mg/kg. 18 patients had adequate onset of sensory/motor blockade for surgical anaesthesia within 30 min. In 2 patients, general anaesthesia was required due to inadequate sensory/motor block for surgery at 30 min post-injection. All patients had complete sensory and motor blockade in all four peripheral nerve distributions immediately post-operatively. Mean duration of sensory/motor block in at least two nerve distributions was 20 h (14–24 h). Time to request for supplemental analgesics was 15 h (9–24 h). No patient demonstated any subjective or objective signs or symptoms of local anaesthetic toxicity.

The results of this study demonstrate the clinical efficacy of 0.5% levobupivacaine for axillary brachial plexus blockade. While the maximum tolerated dose of levobupivacaine for brachial plexus blockade cannot be determined from these results, doses in the range of 3–5 mg/kg were wel tolerated in these patients for axillary block. By comparison, the recommended dose for bupivacaine is 2 mg/kg.

We claim:

1. A unit dosage comprising between 200 mg and 300 mg of levobupivacaine.

2. The dosage according to claim 1, comprising between 225 mg and 300 mg of levobupivacaine.

3. The dosage according to claim 1, comprising between 250 mg and 300 mg of levobupivacaine.

4. A pharmaceutical delivery system comprising between 200 mg and 300 mg of levobupivacaine.

5. The system according to claim 4, comprising between 225 mg and 300 mg of levobupivacaine.

6. The system according to claim 4, comprising between 250 mg and 300 mg of levobupivacaine.

7. The system according to claim 4, which is a syringe.

* * * * *